US00PP26441P2

(12) United States Plant Patent
Mak

(10) Patent No.: US PP26,441 P2
(45) Date of Patent: Mar. 1, 2016

(54) LILY PLANT NAMED 'SUNNY KEYS'

(50) Latin Name: *Lilium hybrida*
Varietal Denomination: Sunny Keys

(71) Applicant: Niels Johannes Cornelis Mak, Wieringerwerf (NL)

(72) Inventor: Niels Johannes Cornelis Mak, Wieringerwerf (NL)

(73) Assignee: Mak Breeding Rights B.V., Wieringerwerf (NL)

( * ) Notice: Subject to any disclaimer, the term of this patent is extended or adjusted under 35 U.S.C. 154(b) by 225 days.

(21) Appl. No.: 13/998,713

(22) Filed: Nov. 26, 2013

(51) Int. Cl.
*A01H 5/02* (2006.01)

(52) U.S. Cl.
USPC ..... Plt./315

(58) Field of Classification Search
USPC ..... Plt./315
See application file for complete search history.

*Primary Examiner* — Anne Grunberg
(74) *Attorney, Agent, or Firm* — C. A. Whealy

(57) ABSTRACT

A new and distinct cultivar of Lily plant named 'Sunny Keys', characterized by its compact and upright plant habit; vigorous growth habit; freely flowering habit; upright flower buds; red purple-colored flowers; and good postproduction longevity.

1 Drawing Sheet

Botanical designation: *Lilium hybrida.*
Cultivar denomination: 'SUNNY KEYS'.

BACKGROUND OF THE INVENTION

The present Invention relates to a new and distinct cultivar of Lily plant, commercially known as Oriental Hybrid Lily, botanically known as *Lilium hybrida* and hereinafter referred to by the name 'Sunny Keys'.

The new Oriental Hybrid Lily plant is a product of a planned breeding program conducted by the Inventor in Wieringerwerf, The Netherlands. The objective of the breeding program is to develop new compact potted Oriental Hybrid Lily plants with healthy foliage, large attractive flowers and good postproduction longevity.

The new Oriental Hybrid Lily plant originated from a cross-pollination in 2003 of two unnamed proprietary seedling selections of *Lilium hybrida*, not patented. The new Oriental Hybrid Lily plant was discovered and selected by the Inventor as a single flowering plant from within the resultant progeny of the stated cross-pollination in a controlled greenhouse environment in Wieringerwerf, The Netherlands in 2006.

Asexual reproduction of the new Oriental Hybrid Lily plant by bulb scales in a controlled greenhouse environment in Wieringerwerf, The Netherlands since 2009 has shown that the unique features of this new Oriental Hybrid Lily plant are stable and reproduced true to type in successive generations.

SUMMARY OF THE INVENTION

Plants of the new Oriental Hybrid Lily have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunny Keys'.

These characteristics in combination distinguish 'Sunny Keys' as a new and distinct Oriental Hybrid Lily plant:

1. Compact and upright plant habit.
2. Vigorous growth habit.
3. Freely flowering habit.
4. Upright flower buds.
5. Red purple-colored flowers.
6. Good postproduction longevity.

Plants of the new Oriental Hybrid Lily differ primarily from plants of the female parent selection in the following characteristics:

1. Plants of the new Oriental Hybrid Lily are more compact than plants of the female parent selection.
2. Plants of the new Oriental Hybrid Lily and the female parent selection differ in flower bud and flower color.

Plants of the new Oriental Hybrid Lily differ primarily from plants of the male parent selection in the following characteristics:

1. Plants of the new Oriental Hybrid Lily are more compact than plants of the male parent selection.
2. Plants of the new Oriental Hybrid Lily have broader leaves than plants of the male parent selection.
3. Plants of the new Oriental Hybrid Lily have smaller flowers than plants of the male parent selection.

Plants of the new Oriental Hybrid Lily can be compared to plants of the Oriental Hybrid Lily 'After Eight', not patented. Plants of the new Oriental Hybrid Lily differ from plants of 'After Eight' in the following characteristics:

1. Plants of the new Oriental Hybrid Lily have darker green-colored leaves than plants of 'After Eight'.
2. Plants of the new Oriental Hybrid Lily flower later than plants of 'After Eight'.
3. Plants of the new Oriental Hybrid Lily have smaller flowers than plants of 'After Eight'.
4. Plants of the new Oriental Hybrid Lily and 'After Eight' differ in flower color as plants of 'After Eight' have dark pink-colored flowers.

DESCRIPTION OF THE PHOTOGRAPH

The accompanying colored photograph illustrates the overall appearance of the new Oriental Hybrid Lily plant showing the colors as true as it is reasonably possible to obtain in colored reproductions of this type. Colors in the photograph may differ slightly from the color values cited in the detailed botanical description which accurately describe the colors of the new Oriental Hybrid Lily plant.

The photograph comprises a side perspective view of a typical flowering plant of 'Sunny Keys' grown in a container.

DETAILED BOTANICAL DESCRIPTION

The aforementioned photograph and following observations and measurements describe plants grown during the spring in 15-cm containers in a glass-covered greenhouse in Wieringerwerf, The Netherlands and under cultural practices typically used in Oriental Hybrid Lily commercial production. During the production of the plants, day temperatures averaged 18° C., night temperatures averaged 15° C. and light levels averaged 6,000 lux. Measurements and numerical values represent averages for typical flowering plants. Plants were 110 days old when the photograph and description were taken. In the following description, color references are made to The Royal Horticultural Society Colour Chart, 2007 Edition, except where general terms of ordinary dictionary significance are used.

Botanical classification: *Lilium hybrida* 'Sunny Keys'.

Parentage:

*Female, or seed, parent*.—Unnamed proprietary seedling selection of *Lilium hybrida,* not patented.

*Male, or pollen, parent*.—Unnamed proprietary seedling selection of *Lilium hybrida,* not patented.

Plant description:

*Plant and growth habit*.—Upright plant habit; single erect flowering stem with a terminal cluster of flowers; compact and dense plant habit; vigorous growth habit.

*Plant height, soil level to top of flowers*.—About 40 cm.

*Plant diameter or spread*.—About 22 cm.

*Plant circumference*.—About 68 cm.

*Bulbs*.—Diameter: About 10 cm to 20 cm. Texture: Smooth. Color: Close to 155D.

*Flowering stems*.—Diameter: About 6 mm to 8 mm. Internode length: About 2 cm to 4 cm. Strength: Strong. Texture: Smooth, glabrous. Color: Towards the base, close to 200B; towards the apex, close to 147A.

*Leaves*.—Arrangement: Alternate, simple; sessile; about 30 leaves develop per plant. Length, upper leaves: About 15 cm. Width, upper leaves: About 6.5 cm. Length, lower leaves: About 10 cm. Width, lower leaves: About 3 cm. Shape: Lanceolate. Apex: Acute. Base: Acutely cuneate. Margin: Entire. Texture, upper and lower surfaces: Glabrous, smooth; leathery. Venation pattern: Parallel. Color: Developing and fully expanded leaves, upper surface: Close to 138A; venation, close to 138A. Developing and fully expanded leaves, lower surface: Close to 137A; venation, close to 137A.

Flower description:

*Flower shape and aspect*.—Flowers umbellate and funnel-shaped; when fully opened, flowers flatten and tepals recurve towards the apex; flower buds face upright and flowers face upright to outwardly.

*Flowering habit*.—Freely flowering habit, large bulbs will produce about four to six flowers per flowering stem.

*Fragrance*.—Slightly fragrant; sweet, pleasant.

*Natural flowering season*.—Plants flower in June and July in The Netherlands; plants can be flowered year-round in the greenhouse and forced to bloom about 110 days after planting bulbs.

*Postproduction longevity*.—Good postproduction longevity, flowers last about two weeks on the plant; tepals not persistent; gynoecium persistent.

*Flower buds*.—Length: About 12 cm. Diameter: About 4.5 cm. Circumference: About 15 cm. Shape: Lanceolate. Color: Close to 149B and 58A; sutures, close to 149B and 58A.

*Flower size*.—Diameter: About 23 cm. Length (height): About 9 cm.

*Perianth*.—Quantity and arrangement: Six tepals per flower arranged in two whorls; tepals imbricate. Tepal length, inner tepals: About 13 cm. Tepal width, inner tepals: About 7.5 cm. Tepal length, outer tepals: About 14 cm. Tepal width, outer tepals: About 5.5 cm. Tepal shape: Lanceolate. Tepal apex: Acute. Tepal margin: Entire. Tepal texture, upper and lower surfaces: Smooth, glabrous. Tepal color: When opening and fully opened, upper surface: Close to 60A; spots, close to 185A; color becoming closer to 59A with development. When opening and fully opened, lower surface: Close to 61A.

*Pedicels*.—Length: About 2 cm. Diameter: About 5 mm. Angle: About 45° to 70° from flowering stem. Strength: Strong. Texture: Smooth, glabrous. Color: Close to 147A.

*Reproductive organs*.—Stamens: Quantity per flower: Six. Filament length: About 7.5 cm. Filament color: Between 145A and NN155D. Anther length: About 2.5 cm. Anther color: Close to 181A. Pollen color: Close to 171B. Pistils: Quantity per flower: One. Style length: About 7.4 cm. Style color: Between 143A and 144D. Stigma diameter: About 6 mm. Stigma shape: Lobed. Stigma color: Close to 79B.

*Fruits*.—Length: About 2 cm. Diameter: About 5 mm. Color: Close to 144D.

*Seeds*.—No viable seeds have been observed on plants of the new Oriental Hybrid Lily.

Disease & pest resistance: Resistance to pathogens and pests common to Oriental Hybrid Lilies has not been observed on plants of the new Oriental Hybrid Lily.

Garden performance: Plants of the new Oriental Hybrid Lily have exhibited good tolerance to rain and wind and have been observed to tolerate temperatures from about −2° C. to about 40° C.

It is claimed:

1. A new and distinct Lily plant named 'Sunny Keys' as illustrated and described.

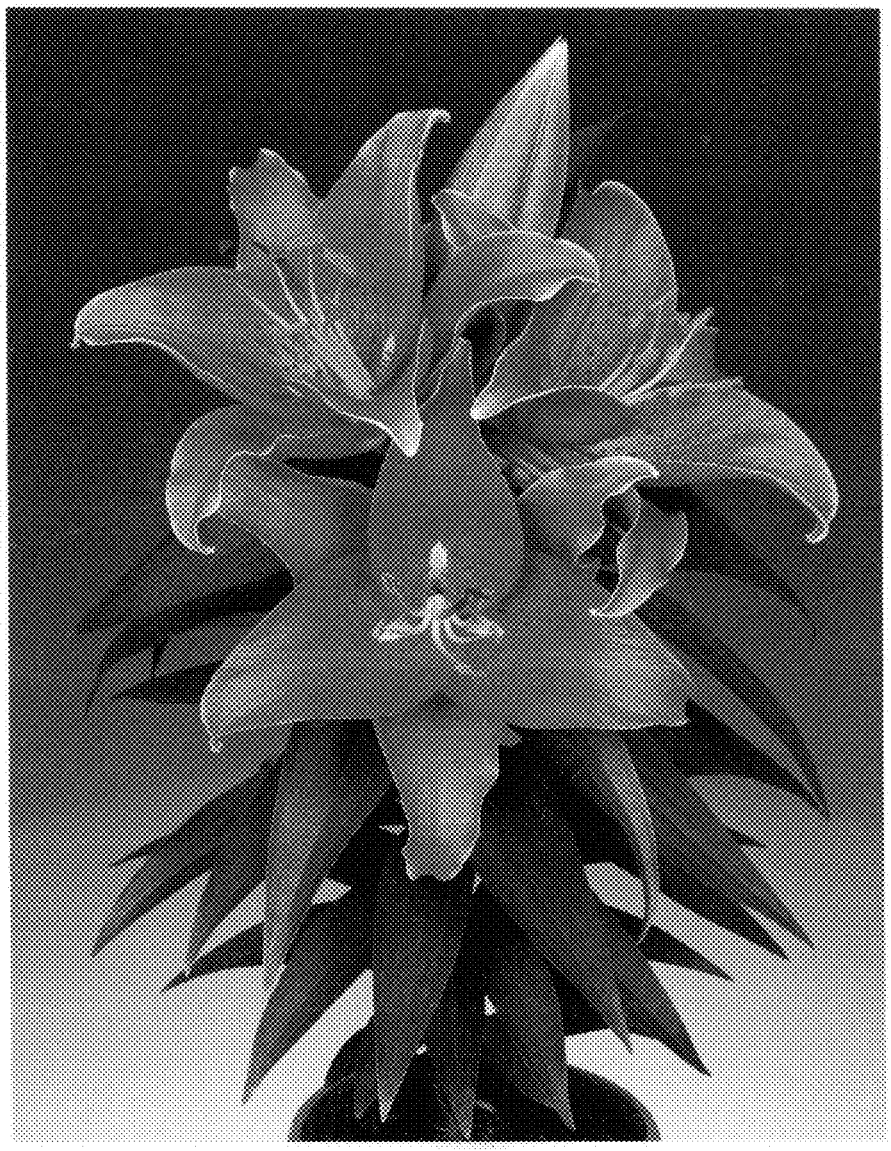

* * * * *